(12) United States Patent
Wu et al.

(10) Patent No.: US 11,773,383 B2
(45) Date of Patent: Oct. 3, 2023

(54) **METHODS FOR PROMOTING EXTRACELLULAR EXPRESSION OF PROTEINS IN *BACILLUS SUBTILIS* USING A CUTINASE**

(71) Applicants: Jing Wu, Wuxi (CN); Lingqia Su, Wuxi (CN); Yan Huang, Wuxi (CN)

(72) Inventors: Jing Wu, Wuxi (CN); Lingqia Su, Wuxi (CN); Yan Huang, Wuxi (CN)

(73) Assignee: Jiangnan University, Wuxi (CN)

( * ) Notice: Subject to any disclaimer, the term of this patent is extended or adjusted under 35 U.S.C. 154(b) by 27 days.

(21) Appl. No.: 17/349,933

(22) Filed: Jun. 17, 2021

(65) Prior Publication Data

US 2022/0135957 A1    May 5, 2022

(30) Foreign Application Priority Data

Nov. 3, 2020  (CN) .......................... 202011208395.6

(51) Int. Cl.
  *C12N 9/92*   (2006.01)
  *C12N 9/18*   (2006.01)
  *C12N 9/10*   (2006.01)
  *C12N 15/75*  (2006.01)

(52) U.S. Cl.
  CPC .............. *C12N 9/18* (2013.01); *C12N 9/1051* (2013.01); *C12N 9/92* (2013.01); *C12N 15/75* (2013.01); *C12Y 204/01245* (2013.01); *C12Y 301/01074* (2013.01); *C12Y 503/01005* (2013.01)

(58) Field of Classification Search
  CPC ...................................................... C12N 9/18
  See application file for complete search history.

(56) References Cited

U.S. PATENT DOCUMENTS

2014/0187468 A1*  7/2014  Estell ................. C11D 3/38627
                                                 510/392

OTHER PUBLICATIONS

Studer. Residue mutations and their impact on protein structure and function: detecting beneficial and pathogenic changes. Biochem. J. (2013) 449, 581-594.*
H6WX58_9ACTN. UnitProtKB Database. Oct. 10, 2018.*
A0A2T0T7X1_9PSEU. UnitProtKB Database. Oct. 10, 2018.*

* cited by examiner

*Primary Examiner* — Yong D Pak
(74) *Attorney, Agent, or Firm* — Lili Chen

(57) ABSTRACT

Disclosed is a method for promoting extracellular expression of proteins in *B. subtilis* using cutinase, which belongs to the technical fields of genetic engineering, enzyme engineering and microbial engineering. It teaches co-expressing a cutinase mutant and a target protein in *B. subtilis* to promote extracellular expression of the target protein which is naturally located inside cells. The target protein includes xylose isomerase, 4,6-α-glucosyltransferase, 4-α-glucosyltransferase, trehalose synthase, branching enzyme and the like. The invention can achieve extracellular expression of intracellularly localized target protein, improve the production efficiency, reduce the production cost and simplify the subsequent extraction process.

5 Claims, No Drawings
Specification includes a Sequence Listing.

SEQUENCE LISTING

<160> NUMBER OF SEQ ID NOS: 10

<210> SEQ ID NO 1
<211> LENGTH: 261
<212> TYPE: PRT
<213> ORGANISM: Artificial Sequence
<220> FEATURE:
<223> OTHER INFORMATION: Protein translated from synthetic DNA

<400> SEQUENCE: 1

Ala Asn Pro Tyr Glu Arg Gly Pro Asn Pro Thr Asp Ala Leu Leu Glu
1               5                   10                  15

Ala Ser Ser Gly Pro Phe Ser Val Ser Glu Glu Asn Val Ser Arg Leu
            20                  25                  30

Ser Ala Ser Gly Phe Gly Gly Gly Thr Ile Tyr Tyr Pro Arg Glu Asn
            35                  40                  45

Asn Thr Tyr Gly Ala Val Ala Ile Ser Pro Gly Tyr Thr Gly Thr Glu
        50                  55                  60

Ala Ser Ile Ala Trp Leu Gly Glu Arg Ile Ala Ser His Gly Phe Val
65                  70                  75                  80

Val Ile Thr Ile Asp Thr Ile Thr Thr Leu Asp Gln Pro Asp Ser Arg
                85                  90                  95

Ala Glu Gln Leu Asn Ala Ala Leu Asn His Met Ile Asn Arg Ala Ser
            100                 105                 110

Ser Thr Val Arg Ser Arg Ile Asp Ser Ser Arg Leu Ala Val Met Gly
            115                 120                 125

His Ser Met Gly Gly Gly Gly Thr Leu Arg Leu Ala Ser Gln Arg Pro
130                 135                 140

Asp Leu Lys Ala Ala Ile Pro Leu Thr Pro Trp His Leu Asn Lys Asn
145                 150                 155                 160

Trp Ser Ser Val Thr Val Pro Thr Leu Ile Ile Gly Ala Asp Leu Asp
                165                 170                 175

Thr Ile Ala Pro Val Ala Thr His Ala Lys Pro Phe Tyr Asn Ser Leu
            180                 185                 190

Pro Ser Ser Ile Ser Lys Ala Tyr Leu Glu Leu Asp Gly Ala Thr His
            195                 200                 205

Phe Ala Pro Asn Ile Pro Asn Lys Ile Ile Gly Lys Tyr Ser Val Ala
210                 215                 220

Trp Leu Lys Arg Phe Val Asp Asn Asp Thr Arg Tyr Thr Gln Phe Leu
225                 230                 235                 240

Cys Pro Gly Pro Arg Asp Gly Leu Phe Gly Glu Val Glu Glu Tyr Arg
                245                 250                 255

Ser Thr Cys Pro Phe
            260

<210> SEQ ID NO 2
<211> LENGTH: 783
<212> TYPE: DNA
<213> ORGANISM: Artificial Sequence
<220> FEATURE:
<223> OTHER INFORMATION: Synthetic DNA

<400> SEQUENCE: 2 gccaaccct  acgagcgcgg  ccccaacccg  accgacgccc  tgctcgaagc  cagcagcggc      60
cccttctccg  tcagcgagga  gaacgtctcc  cggttgagcg  ccagcggctt  cggcggcggc    120
accatctact  cccgcgggga  gaacaacacc  tacggtgcgg  tggcgatctc  ccccggctac    180
accggcactg  aggcttccat  cgcctggctg  ggcgagcgca  tcgcctccca  cggcttcgtc    240
gtcatcacca  tcgacaccat  caccaccctc  gaccagccgg  acagccgggc  agagcagctc    300
aacgccgcgc  tgaaccacat  gatcaaccgg  gcgtcctcca  cggtgcgcag  ccggatcgac    360
agcagccgac  tggcggtcat  gggccactca  atgggcggcg  gcggcaccct  gcgtctggcc    420
tcccagcgtc  ccgacctgaa  ggccgccatc  ccgctcaccc  cgtggcacct  caacaagaac    480
tggagcagcg  tcaccgtgcc  gacgctgatc  atcggggccg  acctcgacac  gatcgcgccg    540

```
gtcgccacgc acgcgaaacc gttctacaac agcctgccga gctccatcag caaggcctac    600
ctggagctgg acggcgcaac ccacttcgcc ccgaacatcc ccaacaagat catcggcaag    660
tacagtgtcg cctggctcaa gcggttcgtc gacaacgaca cccgctacac ccagttcctc    720
tgccccggac cgcgcgacgg actcttcggc gaggtcgaag agtaccgctc cacctgcccg    780
ttc                                                                  783
```

<210> SEQ ID NO 3
<211> LENGTH: 385
<212> TYPE: PRT
<213> ORGANISM: Artificial Sequence
<220> FEATURE:
<223> OTHER INFORMATION: Protein translated from synthetic DNA

<400> SEQUENCE: 3

```
Met Ser Asn Tyr Gln Pro Thr Pro Glu Asp Arg Phe Ser Phe Gly Leu
1               5                   10                  15

Trp Thr Val Gly Trp Arg Gly His Asn Thr Phe Gly Lys Ala Val Arg
            20                  25                  30

Pro Gln Leu Asp Pro Val Asp Val Val Trp Lys Leu Arg Glu Leu Gly
        35                  40                  45

Ala Tyr Gly Ile Thr Phe His Asp Asp Leu Leu Pro Pro Asp Ser
    50                  55                  60

Thr Pro Ala Glu Arg Asp Ala Ile Ile Lys Arg Phe Thr Arg Ala Leu
65                  70                  75                  80

Glu Glu Ser Gly Met Thr Val Pro Met Val Thr Thr Asp Leu Phe Ser
                85                  90                  95

His Pro Val Phe Arg Asp Gly Gly Phe Thr Ser Asn Ser Arg Asp Val
            100                 105                 110

Arg Arg Tyr Ala Leu Arg Lys Val Met Arg Asn Ile Asp Arg Ala Ala
        115                 120                 125

Glu Leu Gly Ala Arg Thr Tyr Val Cys Trp Gly Gly Met Asp Gly Ala
    130                 135                 140

Glu Tyr Glu Pro Ala Lys Asn Ile Ser Ala Ala Leu Asp Arg Leu Arg
145                 150                 155                 160

Glu Ala Phe Asn Ile Leu Cys Glu Tyr Val Arg Ser Lys Gly Tyr Asn
                165                 170                 175

Leu Arg Phe Ala Leu Glu Pro Lys Pro Asn Glu Pro Arg Gly Asp Ile
            180                 185                 190

Leu Leu Pro Thr Ile Gly His Ala Ile Ala Phe Ile Asn Glu Leu Asp
        195                 200                 205

His Pro Glu Met Val Gly Leu Asn Pro Glu Val Gly His Glu Gln Met
    210                 215                 220

Ala Gly Leu Asn Phe Thr His Gly Ile Ala Gln Ala Leu Trp His Gly
225                 230                 235                 240

Lys Leu Phe His Ile Asp Leu Asn Gly Gln Arg Gly Ile Lys Tyr Asp
                245                 250                 255

Gln Asp Leu Arg Phe Gly Ala Gly Asp Val Arg Asp Ala Phe Phe Leu
            260                 265                 270

Val Asn Leu Leu Glu Ser Ser Gly Tyr Asp Gly Pro Arg His Phe Asp
        275                 280                 285

Phe Lys Thr Pro Arg Thr Glu Asp Val Asp Gly Val Trp Glu Ala Ala
    290                 295                 300

Arg Asn Cys Met Arg Asn Tyr Leu Ile Phe Lys Glu Lys Ala Glu Ala
```

Phe Arg Ala Asp Pro Glu Val Arg Glu Ala Met Glu Ala Ala Arg Val
305                 310                 315                 320

Phe Glu Leu Glu Gln Ser Thr Leu Ala Glu Gly Glu Thr Leu Asp Asp
            325                 330                 335

Leu Leu Ala Glu Asp Ile Asn Leu Asp Glu Val Ala Gln Arg Gly Tyr
340                 345                 350

His Phe Glu Arg Leu Asp Gln Leu Ala Leu Asp Tyr Leu Leu Gly Val
    355                 360                 365

Arg
370                 375                 380

385

<210> SEQ ID NO 4
<211> LENGTH: 1158
<212> TYPE: DNA
<213> ORGANISM: Artificial Sequence
<220> FEATURE:
<223> OTHER INFORMATION: Synthetic DNA

<400> SEQUENCE: 4

| atgagcaact | accagcccac | acccgaggac | cggttcagct | tcggactgtg | gactgtggga | 60 |
| tggcgcggcc | acaacacctt | cggcaaggcc | gtacgcccgc | aactcgaccc | cgtcgacgtc | 120 |
| gtctggaaac | tccgcgaact | cggcgcctac | ggcatcacct | tccacgacga | cgacctcctc | 180 |
| ccgccggaca | gcaccccgc | ggaacgcgac | gccatcatca | aacgcttcac | ccgggcgctc | 240 |
| gaagagagcg | gcatgaccgt | ccccatggtc | actaccgacc | tcttcagcca | cccgtcttc  | 300 |
| cgcgacggcg | gcttcacctc | caacagccgc | gacgtgcgcc | gctacgccct | gcgcaaggtc | 360 |
| atgcgcaaca | tcgaccgcgc | cgcggaactc | ggcgcccgca | cctacgtgtg | ctggggcggc | 420 |
| atggacggcg | ccgaatacga | acccgccaag | aacatctccg | ccgcgctcga | ccgcctgcgc | 480 |
| gaagccttca | acatcctgtg | cgaatacgtc | gcagcaagg  | gctacaacct | gcggttcgcc | 540 |
| ctcgaaccca | aacccaacga | gccccgcggc | gacatcctcc | tgcccaccat | cggccacgcc | 600 |
| atcgccttca | tcaacgagct | cgaccacccc | gaaatggtcg | gcctcaaccc | cgaagtcggc | 660 |
| cacgaacaga | tggccggact | caacttcacc | cacggcatcg | cccaagccct | ctggcacggg | 720 |
| aaactgttcc | acatcgacct | caacggccag | cgcggcatca | aatacgacca | ggacctgcgc | 780 |
| ttcggcgccg | gcgacgtgcg | cgacgcgttc | ttcctcgtca | acctgctgga | aagcagtggc | 840 |
| tacgacggac | cgcgccactt | cgacttcaag | accccgcgca | ccgaagacgt | cgacggcgtg | 900 |
| tgggaagcgg | cacgcaactg | catgcgcaac | tacctcatct | tcaaggagaa | ggctgaagcg | 960 |
| ttccgcgccg | accccgaagt | ccgcgaagcc | atggaagccg | cccgggtctt | cgaactggag | 1020 |
| cagtccaccc | tcgccgaagg | ggagaccctg | gacgacctgc | tcgccgaaga | catcaacctg | 1080 |
| gacgaagtgg | cccagcgcgg | ctaccacttc | gaacgcctcg | accagctcgc | cctcgactac | 1140 |
| ctcctgggcg | tgcgctaa   |            |            |            |            | 1158 |

<210> SEQ ID NO 5
<211> LENGTH: 1151
<212> TYPE: PRT
<213> ORGANISM: Artificial Sequence
<220> FEATURE:
<223> OTHER INFORMATION: Protein translated from synthetic DNA

<400> SEQUENCE: 5

Met Phe Gly Asn Asp Gly Arg Ile Ala Thr Lys Val Thr Pro Trp Ala
1               5                   10                  15

```
Gly Thr Tyr Tyr Tyr Phe Asp Pro Leu Thr Tyr Leu Arg Val Asp Asn
                20              25                  30

Asn Tyr Val Gln Ser Gln Trp Gly Leu Trp Tyr Met Phe Gly Asn Asp
        35              40                  45

Gly Arg Val Gln Ser Gly Val Gln Arg Trp Ser Gly Thr Tyr Tyr Tyr
    50              55                  60

Phe Asp Pro Thr Thr Tyr Leu Arg Val Asp Asp Tyr Val Thr Ser
65              70                  75                  80

Gln Trp Gly Leu Lys Tyr Met Phe Gly Lys Asp Gly Arg Ile Val Ser
            85                  90                  95

Asp Leu Tyr Lys Trp Asp Lys Lys Asn Gln Trp Tyr Tyr Phe Asp Pro
                100                 105                 110

Val Thr Tyr Leu Ala Val Thr Asn Asn Tyr Ile Lys Ala Asn Asp Gly
            115                 120                 125

Asn Trp Tyr Leu Phe Thr Ala Asp Gly Thr Ala Ala Ser Lys Val Ala
    130                 135                 140

Pro Trp Ser Gly Thr Tyr Tyr Phe Asp Pro Val Thr His Leu Arg
145                 150                 155                 160

Val Asp Asn Asp Tyr Val Gln Ser Gln Trp Gly Asp Trp Tyr Met Phe
                165                 170                 175

Gly Asn Asp Gly Arg Ile Val Thr Gly Pro Val Thr Trp Tyr Gly Ser
            180                 185                 190

Asn Tyr Tyr Phe Asp Pro Thr Thr Tyr Leu Lys Val Thr Asn Arg Trp
        195                 200                 205

Ile Asn Asp Lys Tyr Tyr Gly Ser Asp Gly Arg Gln Ala Val Ser Gln
    210                 215                 220

Ser Glu Lys Ile Asn Asn Lys Phe Tyr Tyr Phe Asp Glu Asn Gly Ser
225                 230                 235                 240

Ile Ile Arg Asn Gln Phe Lys Lys Ile Asn Gly Thr Tyr Tyr Phe
            245                 250                 255

Gly Asp Asp Gly Ala Ala Leu Ile Gly Leu His Val Ile Asp Gly Lys
            260                 265                 270

Asn Tyr Asn Phe Ala Ser Asp Gly Gln Leu Leu Gly Lys Thr Tyr Gly
        275                 280                 285

Lys Ile Glu Asn Gly Lys Phe Asn Ile Tyr Asp Ala Thr Ser Asn Lys
    290                 295                 300

Leu Leu Lys Thr Leu Asp Ser Gly Asp Trp Glu Asn Leu Ala Asp Ser
305                 310                 315                 320

Phe Asp Ser Ser Ser Ile Asn Asn Ile Asp Gly Tyr Leu Ser Tyr Gly
                325                 330                 335

Gly Trp Tyr Arg Pro Tyr Gly Thr Ser Gln Asp Gly Lys Thr Trp His
            340                 345                 350

Lys Thr Thr Ala Ser Asp Trp Arg Pro Leu Leu Met Tyr Val Tyr Pro
        355                 360                 365

Ser Lys Asp Val Glu Ala Lys Tyr Ile Lys Tyr Phe Val Ser Asn Gly
    370                 375                 380

Tyr Thr Asn Thr Asp Tyr Gly Leu Thr Lys Asp Asn Val Ala Asn Leu
385                 390                 395                 400

Ser Gln Asp Thr Asp Ser Ala Thr Leu Asn Lys Tyr Ala Arg Asn Leu
            405                 410                 415

Arg Phe Val Ile Glu Lys Ser Ile Ala Ile Asn Lys Ser Thr Ser Pro
            420                 425                 430
```

-continued

Leu Ala Asn Asp Ile Asn Lys Phe Met Thr Thr Ile Pro Glu Leu Ser
435                 440                 445

Ala Lys Ser Glu Leu Pro Ser Tyr Ser Gln Asn Asp Gln Leu Val Phe
450                 455                 460

Val Asn Asn Ser Ser Asn Gln Ala Lys Gly Asn Thr Ser Tyr Ala
465             470              475                  480

Asp Ser Asn Tyr Arg Leu Met Asp Arg Thr Leu Asn Asn Gln Thr Asn
                485             490                 495

Asn Asp Ser Ser Asp His Ser Pro Glu Met Leu Leu Gly Asn Asp Ile
            500                 505                 510

Asp Asn Ser Asn Pro Val Val Gln Ala Glu Asn Leu Asn Trp Glu Tyr
            515                 520                 525

Phe Leu Leu Asn Tyr Gly Lys Leu Met Gln Tyr Asn Ala Asn Ala Ser
            530                 535                 540

Val Asn Gly Asn Phe Asp Gly Phe Arg Val Asp Ala Ala Asp His Ile
545                 550                 555                 560

Asp Ala Asp Val Leu Asp Gln Leu Gly Gln Leu Met Asn Asp Leu Tyr
                565                 570                 575

His Thr Lys Gly Asn Gln Val Asn Ala Asn Ser His Leu Val Tyr Asn
                580                 585                 590

Glu Gly Tyr Asn Tyr Gly Asp Leu Arg Met Leu Asn Gly Lys Asn Asn
            595                 600                 605

Pro Ala Leu Tyr Leu Asp Ser Gly Tyr Trp Ser Gln Leu Glu Ser Ser
            610                 615                 620

Leu Gly Arg Asn Ala Asp Asn Arg Asp Ser Ile Ser Asn Leu Met Thr
625                 630                 635                 640

Asn Ser Ile Val Asn Arg Ala Asn Asp Val Thr Glu Asn Thr Ala Thr
                645                 650                 655

Pro Asn Trp Ser Phe Val Thr Asn His Asp Gln Arg Asn Asn Leu Val
            660                 665                 670

Asn Arg Ile Val Tyr Asp Lys Asp Ile Thr Ala Gln Lys Ala Trp Asp
            675                 680                 685

Met Phe Tyr Ala Asp Gln Ala Lys Thr Asp Lys Gln Tyr Ala Gln Tyr
690                 695                 700

Asn Met Pro Ala Gln Tyr Ala Leu Leu Leu Ser Asn Lys Asp Thr Val
705                 710                 715                 720

Pro Gln Val Tyr Tyr Gly Asp Leu Tyr Asn Glu Thr Asp Gln Tyr Met
                725                 730                 735

Lys Thr Lys Ser Met Tyr Tyr Asp Ala Ile Thr Thr Leu Met Lys Ala
            740                 745                 750

Arg Arg Thr Phe Val Asn Gly Gln Thr Met Thr Lys Leu Asn Asn
            755                 760                 765

Asn Leu Ile Ala Ser Val Arg Tyr Gly Lys Gly Val Ser Asp Ala Ser
            770                 775                 780

Gly Lys Gly Thr Asp Ser Leu Ser Arg Thr Thr Gly Met Ala Val Ile
785                 790                 795                 800

Val Gly Asn Asn Pro Thr Met Ser Glu Gln Val Val Gln Ile Asn Met
                805                 810                 815

Gly Val Ala His Ala Asn Glu Gln Tyr Arg Ser Leu Ile Asn Ser Thr
                820                 825                 830

Asp Asn Gly Leu Thr Tyr Asp Gly Met Gly Ser Thr Phe Leu Thr Thr
            835                 840                 845

Asp Ser Lys Gly Ile Leu Arg Val Thr Val Lys Gly Tyr Ser Asn Pro

```
                850                 855                 860
Tyr Val Asn Gly Tyr Leu Ser Val Trp Val Pro Val Ile Ser Gly Thr
865                 870                 875                 880

Gln Asn Ala Gln Thr Asn Ala Gln Glu Val Asn Asn Val Ser Gly Lys
                885                 890                 895

Thr Phe Ala Ser Asn Ala Ala Leu Asp Ala His Met Ile Tyr Gln Asp
            900                 905                 910

Phe Ser Leu Ala Gln Pro Glu Pro Thr Thr Ile Asn Asn His Ala Tyr
        915                 920                 925

Asn Val Ile Lys Ala Asn Ala Ala Leu Phe Asn Gln Leu Gly Ile Thr
    930                 935                 940

Asp Phe Trp Met Ala Pro Ala Tyr Met Pro Val Asn Ser Ser Lys Tyr
945                 950                 955                 960

Gln Asp Gly Tyr Ala Thr Asp Asp Arg Tyr Asn Leu Gly Thr Thr Asp
                965                 970                 975

Asn Pro Thr Lys Tyr Gly Ser Gly Glu Glu Leu Ala Asn Ala Ile Ala
            980                 985                 990

Ala Leu His Gln Glu Gly Leu Lys  Val Gln Glu Asp Leu  Val Met Asn
        995                 1000                1005

Gln Met  Phe Gly Phe Pro Ser  Gln Glu Ala Val Thr  Val Thr Arg
    1010                1015                1020

Ala Asp  Ser Tyr Gly Lys Gln  Phe Tyr Val Asp Gly  Lys Thr Phe
    1025                1030                1035

Ala Asn  Gln Ile Tyr Phe Gly  Tyr Thr Arg Asn Gly  Ser Gln Asn
    1040                1045                1050

Gln Gln  Gln Asn Tyr Gly Gly  Arg Tyr Leu Gly Glu  Leu Asn Gln
    1055                1060                1065

Lys Tyr  Pro Asp Leu Phe Thr  Thr Lys Ala Ala Ser  Ser Gly Val
    1070                1075                1080

Ala Pro  Asp Pro Asn Thr Arg  Ile Thr Glu Trp Ser  Ala Lys Tyr
    1085                1090                1095

Glu Asn  Gly Thr Ser Leu Gln  Asn Val Gly Val Gly  Leu Ala Ile
    1100                1105                1110

Lys Met  Pro Asn Gly Tyr Tyr  Ala Tyr Leu Asn Asn  Gly Ser Asn
    1115                1120                1125

Lys Thr  Phe Asn Thr Thr Leu  Pro Asp Ala Ile Ala  Ser Val Asp
    1130                1135                1140

Tyr Tyr  Ala Asn Lys Ala Asp  Leu
    1145                1150

<210> SEQ ID NO 6
<211> LENGTH: 3462
<212> TYPE: DNA
<213> ORGANISM: Artificial Sequence
<220> FEATURE:
<223> OTHER INFORMATION: Synthetic DNA

<400> SEQUENCE: 6
atgtttggta atgatggccg tattgcaacc aaagtgacac cgtgggccgg cacctattat      60
tactttgatc ctctgaccta tctgcgtgtt gacaataatt atgtgcaatc tcagtggggt     120
ctgtggtaca tgttcggcaa cgatggccgt gttcagtcag gtgtacagcg ctggagcggt     180
acgtattatt atttcgaccc taccacctat ctgcgcgttg atgacgatta tgttacatct     240
cagtggggac tgaaatacat gtttggcaaa gatggtcgta ttgtttctga tctgtataaa     300
```

```
tgggacaaaa agaatcagtg gtattatttc gatccggtga cctatctggc agttaccaac    360
aattatatta aagccaacga tgggaattgg tatctgttca ccgcagatgg tacggcagcg    420
agcaaagtgg caccgtggag cggtacctat tactattttg accctgttac ccatctgcgt    480
gtcgataatg attatgttca gtcacagtgg ggtgattggt atatgttcgg caatgatggt    540
cgtatcgtta ccgggccggt tacctggtat ggcagcaatt attattttga cccgaccacc    600
tatctgaaag ttacgaatcg ttggattaat gataaatact acggtagtga cggtcgtcag    660
gcagttagcc agagcgagaa aattaataac aaatttttact acttcgacga aacggcagc    720 attattcgta accagtttaa aaagatcaac ggcggcacct attactttgg agatgatgga    780
gcagcactga ttggactgca cgttatcgat ggtaaaaatt ataatttcgc cagcgatggt    840
cagctgctgg gtaaaacata cggtaaaatt gaaaacggaa aattcaacat ctacgatgca    900
accagcaaca aactgctgaa acactggat agcggtgatt gggagaatct ggcagatagc    960
tttgatagta gcagcattaa taacatcgat ggctatctga gctatggtgg gtggtatcgc    1020
ccgtacggta cctctcagga cggtaaaaca tggcataaaa ccacagcaag cgattggcgt    1080
ccgctgctga tgtacgtgta cccgagcaaa gacgttgaag cgaaatatat taaatacttc    1140
gtgagcaacg gtatacaaa tacagactac ggtctgacca agataacgt ggcgaatctg     1200 agccaagaca ccgatagcgc aaccctgaat aaatatgcac gcaatctgcg cttcgttatt    1260
gaaaaatcaa ttgcaattaa caaaagcacg agcccgctgg caaacgatat taacaaattc    1320
atgaccacca ttccggaact gtctgcaaaa tccgaactgc cgtcttattc tcagaacgat    1380
caactggttt ttgtgaacaa taacagcagc aatcaagcaa aaggtaacac cagctatgcc    1440 gactcaaaact accgtctgat ggatcgtacc ctgaataatc agaccaataa cgacagcagc    1500
gaccatagcc cggaaatgct gctgggaaac gacattgata tagcaatcc agttgttcag    1560 gccgaaaatc tgaattggga atatttttctg ctgaactacg gcaaactgat gcagtacaac    1620
gcaaacgcaa gcgtgaatgg taatttcgat ggctttcgcg tcgatgccgc agatcatatc    1680
gatgcagatg ttctggatca gctgggtcaa ctgatgaatg atctgtacca taccaaaggt    1740
aaccaagtta atgccaatag ccatctggtg tataatgaag gttataatta cggtgacctg    1800
cgtatgctga atggtaaaaa taatccggca ctgtacctgg atagcggcta ttggagccag    1860
ctggagtcca gcctgggacg taatgcggac aaccgtgatt ccattagtaa tctgatgacc    1920
aactccatcg tgaatcgcgc aaatgatgtt accgaaaata cagcaacccc gaattggagc    1980
tttgttacaa accatgatca gcgtaataat ctggttaatc gtattgttta cgacaaagac    2040
attaccgcgc agaaagcatg ggatatgttt tatgcagacc aggcaaaaac cgataaacag    2100
tatgcacagt acaatatgcc tgcacagtat gcactgctgc tgagcaacaa agataccgtg    2160
ccacaggtat actatgggga tctgtataat gaaaccgatc aatatatgaa aaccaaaagc    2220
atgtactacg acgcgattac caccctgatg aaagcccgtc gtacattcgt gaatggtggt    2280
caaaccatga ccaaactgaa taataacctg attgcatccg ttcgctatgg caaaggcgtt    2340
tcggatgcaa gtggcaaagg caccgacagc ctgagccgta ccaccggtat ggcagtgatc    2400
gttggtaata cccgaccat gagcgaacag gttgttcaga ttaatatggg tgttgcacat    2460
gcaaatgaac agtaccgtag cctgatcaat agcaccgaca acggactgac ctatgacggg    2520
atgggcagca ccttcctgac cactgatagt aaaggtatcc tgcgtgttac cgtaaaaggt    2580
tacagcaatc cgtatgttaa tggctacctg agcgtttggg ttcctgttat tagcggtacc    2640
cagaatgcac agaccaacgc acaggaagtg aataatgtta gcgggaaaac attcgcaagc    2700
```

```
aatgcagcac tggatgcaca catgatttat caagacttta gcctggccca gccggaacca    2760
accaccatca ataaccacgc atataatgtt atcaaagcaa atgcagcact gtttaatcag    2820
ctgggtatta ccgattttg gatggccccg gcatatatgc ctgttaattc aagcaaatat     2880
caggacggat atgcaaccga tgaccgttac aatctgggta caacagataa tccgaccaaa    2940
tatggcagcg agaggagct ggcaaatgca attgccgcac tgcaccagga aggtctgaaa     3000
gtgcaggaag atctggtgat gaatcagatg tttgggttcc cgagtcagga agcagtgacg    3060
gttacccgtg cagatagcta tggcaaacag ttttatgtgg atggtaaaac attcgccaat    3120
caaatttatt tcggttacac acgtaacggt agccagaatc agcaacgaa ttatggtggg     3180 cgctatctgg gtgaactgaa tcagaaatat ccggatctgt ttaccaccaa agcagcaagt    3240
agcggtgttg caccagatcc taacacccgt attaccgaat ggagcgcaaa atatgaaaat    3300
gggaccagcc tgcaaaatgt aggcgtgggt ctggccatta aaatgccgaa tggatattat    3360
gcatacctga ataatggtag caataaaaca ttcaacacca ccctgccgga tgcaatcgca    3420
agcgttgatt actacgcgaa taaagcagat ctgtaaggat cc                       3462
```

<210> SEQ ID NO 7
<211> LENGTH: 484
<212> TYPE: PRT
<213> ORGANISM: Artificial Sequence
<220> FEATURE:
<223> OTHER INFORMATION: Protein translated from synthetic DNA

<400> SEQUENCE: 7

```
Met Arg Leu Ala Gly Ile Leu Leu His Val Thr Ser Leu Pro Ser Pro
1               5                   10                  15

Tyr Gly Ile Gly Asp Leu Gly Lys Glu Ala Tyr Arg Phe Leu Asp Phe
            20                  25                  30

Leu Lys Glu Cys Gly Phe Ser Leu Trp Gln Val Leu Pro Leu Asn Pro
        35                  40                  45

Thr Ser Leu Glu Ala Gly Asn Ser Pro Tyr Ser Ser Asn Ser Leu Phe
    50                  55                  60

Ala Gly Asn Tyr Val Leu Ile Asp Pro Glu Glu Leu Leu Glu Glu Asp
65                  70                  75                  80

Leu Ile Lys Glu Arg Asp Leu Lys Arg Phe Pro Leu Gly Glu Ala Leu
                85                  90                  95

Tyr Glu Val Val Tyr Glu Tyr Lys Lys Glu Leu Leu Glu Lys Ala Phe
            100                 105                 110

Lys Asn Phe Arg Arg Phe Glu Leu Leu Glu Asp Phe Leu Lys Glu His
        115                 120                 125

Ser Tyr Trp Leu Arg Asp Tyr Ala Leu Tyr Met Ala Ile Lys Glu Glu
    130                 135                 140

Glu Gly Lys Glu Trp Tyr Glu Trp Asp Glu Glu Leu Lys Arg Arg Glu
145                 150                 155                 160

Lys Glu Ala Leu Lys Arg Val Leu Asn Lys Leu Lys Gly Arg Phe Tyr
                165                 170                 175

Phe His Val Phe Val Gln Phe Val Phe Phe Lys Gln Trp Glu Lys Leu
            180                 185                 190

Arg Arg Tyr Ala Arg Glu Arg Gly Ile Ser Ile Val Gly Asp Leu Pro
        195                 200                 205

Met Tyr Pro Ser Tyr Ser Ser Ala Asp Val Trp Thr Asn Pro Glu Leu
    210                 215                 220
```

```
Phe Lys Leu Asp Gly Asp Leu Lys Pro Leu Phe Val Ala Gly Val Pro
225                 230                 235                 240

Pro Asp Phe Phe Ser Lys Thr Gly Gln Leu Trp Gly Asn Pro Val Tyr
            245                 250                 255

Asn Trp Glu Glu His Glu Lys Glu Gly Phe Arg Trp Trp Ile Arg Arg
        260                 265                 270

Val His His Asn Leu Lys Leu Phe Asp Phe Leu Arg Leu Asp His Phe
    275                 280                 285

Arg Gly Phe Glu Ala Tyr Trp Glu Val Pro Tyr Gly Glu Glu Thr Ala
290                 295                 300

Val Asn Gly Arg Trp Val Lys Ala Pro Gly Lys Thr Leu Phe Lys Lys
305                 310                 315                 320

Leu Leu Ser Tyr Phe Pro Lys Asn Pro Phe Ile Ala Glu Asp Leu Gly
            325                 330                 335

Phe Ile Thr Asp Glu Val Arg Tyr Leu Arg Glu Thr Phe Lys Ile Pro
            340                 345                 350

Gly Ser Arg Val Ile Glu Phe Ala Phe Tyr Asp Lys Glu Ser Glu His
        355                 360                 365

Leu Pro His Asn Val Glu Glu Asn Val Tyr Tyr Thr Ser Thr His
370                 375                 380

Asp Leu Pro Pro Ile Arg Gly Trp Phe Glu Asn Leu Gly Glu Glu Ser
385                 390                 395                 400

Arg Lys Arg Leu Phe Glu Tyr Leu Gly Arg Glu Ile Lys Glu Lys
                405                 410                 415

Val Asn Glu Glu Leu Ile Arg Leu Val Leu Ile Ser Arg Ala Lys Phe
            420                 425                 430

Ala Ile Ile Gln Met Gln Asp Leu Leu Asn Leu Gly Asn Glu Ala Arg
            435                 440                 445

Met Asn Tyr Pro Gly Arg Pro Phe Gly Asn Trp Arg Trp Ile Lys
        450                 455                 460

Glu Asp Tyr Thr Gln Lys Lys Glu Phe Ile Lys Lys Leu Leu Gly Ile
465                 470                 475                 480

Tyr Gly Arg Glu

<210> SEQ ID NO 8
<211> LENGTH: 1458
<212> TYPE: DNA
<213> ORGANISM: Artificial Sequence
<220> FEATURE:
<223> OTHER INFORMATION: Synthetic DNA

<400> SEQUENCE: 8
atgagattgg caggtatttt acttcacgta acttcacttc cctctcctta cgggataggg    60
gatctcggaa aagaagccta caggtttctg gacttcttaa aggagtgcgg ttttagcctt   120
tggcaggttc tacctctgaa ccccacttca cttgaggcgg gaaactcacc ctacagttca   180
aactccctct tcgcgggcaa ttacgtacta atagaccctg aagaattatt ggaggaggac   240
ttaataaaag aagggacttt aaaaagattt cccttgggtg aagcccttta cgaagtcgtg   300
tacgagtata aaaagagtt gctcgaaaaa gcctttaaaa atttcaggag atttgaactg   360
cttgaagatt ttctgaagga acactcttac tggctcagag attacgcact ttacatggct   420
ataaaagaag aagagggaaa ggagtggtat gaatgggatg aagaattgaa gaggagagaa   480
aaagaggctt taaaagggt gttaaataag ttaaagggga ggttttactt ccacgtattc   540
gtccagtttg ttttcttcaa gcagtgggaa aaactgagaa gatacgcaag ggaaaggggg   600
```

```
ataagcatag ttggagatct tccaatgtac ccctcgtact caagtgcgga cgtgtggaca    660
aatcctgaac ttttaaaact ggacggagat ttaaaacccc ttttgtagc gggtgttcct     720 cctgattttt tcagtaaaac gggacagctg tggggaaatc ccgtttacaa ctgggaagaa    780
cacgaaaagg aaggcttcag atggtggata aggagagttc atcacaactt aaaactcttt    840
gactttttaa gacttgacca cttcaggga tttgaggcgt actgggaggt tccttacggt     900
gaagaaactg cggtaaacgg aaggtgggta aaggctcccg aaagacact atttaaaaaa    960 ctcttatcat acttcccgaa gaacccattc atagcggagg acttaggttt tataacggac   1020
gaagtgaggt acttgaggga aacttttaaa atcccgggaa gcagagttat tgagtttgcc   1080
ttctacgata aggaaagtga gcaccttccc cacaacgttg aagagaacaa cgtttactac   1140
acttcaactc atgaccttcc tccgataaga ggatggtttg agaatttagg agaagaatca   1200
agaaaacgat tatttgaata cttgggaagg gagattaaag aggaaaaagt taacgaggag   1260
cttataagac tcgttttaat tcaagggcg aagttcgcaa taatccagat gcaggactta   1320
ctcaatctcg gcaatgaagc gaggatgaat tacccccggaa gacctttcgg aaattggagg   1380
tggagaataa aggaagatta cacacaaaag aaggaattta ttaaaaaact cctcggaatt   1440
tacggaagag aagtttaa                                                 1458

<210> SEQ ID NO 9
<211> LENGTH: 606
<212> TYPE: PRT
<213> ORGANISM: Artificial Sequence
<220> FEATURE:
<223> OTHER INFORMATION: Protein translated from synthetic DNA

<400> SEQUENCE: 9

Met Thr Thr Gln Pro Ala Pro Gly Ala Arg Pro Thr Pro Thr Gly Ser
1               5                   10                  15

Val Pro Asp Thr Phe Thr His Ala Lys Pro Arg Asp Pro Tyr Trp Tyr
            20                  25                  30

Lys His Ala Val Phe Tyr Glu Val Leu Val Arg Gly Phe Tyr Asp Ser
        35                  40                  45

Asn Gly Asp Gly Thr Gly Asp Leu Arg Gly Leu Ile Glu Lys Leu Asp
    50                  55                  60

Tyr Leu Gln Trp Leu Gly Ile Asp Cys Leu Trp Leu Pro Ile Tyr
65                  70                  75                  80

Glu Ser Pro Leu Arg Asp Gly Gly Tyr Asp Val Ser Asp Tyr Met Lys
                85                  90                  95

Ile Leu Pro Glu Phe Gly Arg Ile Ser Asp Phe Val Glu Leu Val Glu
            100                 105                 110

Lys Ala His Gln Arg Gly Ile Arg Val Ile Thr Asp Leu Val Met Asn
        115                 120                 125

His Thr Ser Asp Gln His Pro Trp Phe Gln Ala Ser Arg His Asp Pro
    130                 135                 140

Asp Gly Pro Tyr Gly Asn Phe Tyr Val Trp Ser Asp Thr Thr Glu Arg
145                 150                 155                 160

Tyr Ser Asp Ala Arg Ile Ile Phe Ile Asp Thr Glu Gln Ser Asn Trp
                165                 170                 175

Thr Tyr Asp Glu Val Arg Gly Gln Tyr Tyr Trp His Arg Phe Phe Ser
            180                 185                 190

His Gln Pro Asp Leu Asn Phe Glu Asn Pro Asp Val Gln Asp Ala Ile
        195                 200                 205
```

Leu Glu Val Met Arg Phe Trp Leu Asp Leu Gly Ile Asp Gly Phe Arg
            210                 215                 220

Leu Asp Ala Val Pro Tyr Leu Tyr Glu Arg Glu Gly Thr Asn Cys Glu
225                 230                 235                 240

Asn Leu Lys Glu Thr His Glu Phe Leu Lys Arg Ile Arg Ala Glu Val
            245                 250                 255

Asp Arg Leu Tyr Pro Asp Arg Val Leu Leu Ser Glu Ala Asn Gln Trp
            260                 265                 270

Pro Ala Asp Val Val Asp Tyr Phe Gly Asp Tyr Glu Ser Gly Gly Asp
            275                 280                 285

Glu Cys His Met Asn Phe His Phe Pro Leu Met Pro Arg Met Phe Met
            290                 295                 300

Ala Val Arg Arg Glu Gln Arg Tyr Pro Ile Ser Glu Ile Leu Ala Gln
305                 310                 315                 320

Thr Pro Pro Ile Pro Arg Asn Cys Gln Trp Ala Ile Phe Leu Arg Asn
            325                 330                 335

His Asp Glu Leu Thr Leu Glu Met Val Ser Asp Glu Arg Asp Tyr
            340                 345                 350

Met Tyr Ser Glu Tyr Ala Lys Asp Pro Arg Met Arg Ala Asn Met Gly
            355                 360                 365

Ile Arg Arg Arg Leu Ala Pro Leu Leu Glu Asn Asp Leu Asn Gln Ile
            370                 375                 380

Lys Leu Phe Thr Ala Leu Leu Leu Ser Leu Pro Gly Ser Pro Val Leu
385                 390                 395                 400

Tyr Tyr Gly Asp Glu Ile Gly Met Gly Asp Asn Ile Trp Leu Gly Asp
            405                 410                 415

Arg Asp Ser Val Arg Thr Pro Met Gln Trp Thr Pro Asp Arg Asn Ala
            420                 425                 430

Gly Phe Ser Arg Cys Asp Pro Gly Arg Leu Tyr Leu Pro Val Ile Met
            435                 440                 445

Asp Pro Ile Tyr Gly Tyr Gln Ala Ile Asn Val Glu Ala Gln Gln Asn
450                 455                 460

Asn Pro Asn Ser Leu Leu Asn Trp Thr Arg Asn Met Ile Gln Ile Arg
465                 470                 475                 480

Lys Gln His Pro Val Phe Gly Thr Gly Asp Phe Thr Glu Leu His Ala
            485                 490                 495

Ser Asn Pro Ser Val Phe Ala Phe Val Arg Glu Tyr Gly Asp Asp Arg
            500                 505                 510

Met Leu Cys Val Asn Asn Leu Ser Arg Phe Pro Gln Pro Val Glu Leu
            515                 520                 525

Asp Leu Arg Arg Phe Glu Gly Ile Thr Pro Ile Glu Cys Thr Gly Gly
530                 535                 540

Val His Phe Pro Pro Ile Gly Glu Leu Pro Tyr Leu Leu Thr Leu Pro
545                 550                 555                 560

Gly His Gly Phe Tyr Trp Phe Gln Leu Pro Val Ala Glu Glu Gln
            565                 570                 575

Pro Leu Ala Gln Pro Val Thr Thr Val Pro Ala Pro Gln Pro Pro
            580                 585                 590

Ala Pro Ala Asp Arg Pro Ala Ser Asp Pro Thr Gln Arg Ser
            595                 600                 605

<210> SEQ ID NO 10
<211> LENGTH: 520

<212> TYPE: PRT
<213> ORGANISM: Artificial Sequence
<220> FEATURE:
<223> OTHER INFORMATION: Protein translated from synthetic DNA

<400> SEQUENCE: 10

Met Ala Arg Phe Ala Leu Val Leu His Ala His Leu Pro Tyr Val Arg
1               5                   10                  15

Ala His Gly Met Trp Pro Phe Gly Glu Glu Thr Leu Tyr Glu Ala Met
            20                  25                  30

Ala Glu Thr Tyr Leu Pro Leu Ile Arg Val Leu Glu Arg Leu Arg Ala
        35                  40                  45

Glu Gly Val Glu Ala Pro Phe Thr Leu Gly Ile Thr Pro Ile Leu Ala
    50                  55                  60

Glu Gln Leu Ala Asp Ala Arg Ile Lys Glu Gly Phe Trp Ala Tyr Ala
65                  70                  75                  80

Lys Asp Arg Leu Glu Arg Ala Gln Gly Asp Tyr Gln Arg Tyr Arg Gly
                85                  90                  95

Thr Ala Leu Glu Ala Ser Ala Arg His Gln Val Ala Phe Trp Glu Leu
            100                 105                 110

Thr Leu Asp His Phe Gln Arg Leu Ser Gly Asp Leu Val Ala Ala Phe
        115                 120                 125

Arg Lys Ala Glu Glu Gly Gly Gln Val Glu Leu Ile Thr Ser Asn Ala
    130                 135                 140

Thr His Gly Tyr Ser Pro Leu Leu Gly Tyr Asp Glu Ala Leu Trp Ala
145                 150                 155                 160

Gln Ile Lys Thr Gly Val Ser Thr Tyr Arg Arg His Phe Ala Lys Asp
                165                 170                 175

Pro Thr Gly Phe Trp Leu Pro Glu Met Ala Tyr Arg Pro Lys Gly Pro
            180                 185                 190

Trp Lys Pro Pro Val Glu Gly Pro Glu Gly Val Arg Pro Gly Val
        195                 200                 205

Asp Glu Leu Leu Met Arg Ala Gly Ile Arg Tyr Thr Phe Val Asp Ala
    210                 215                 220

His Leu Val Gln Gly Gly Glu Pro Leu Ser Pro Tyr Gly Glu Ala Ala
225                 230                 235                 240

Leu Gly Pro Val Glu Ser Gln Glu Ala Thr Tyr His Val His Glu Leu
                245                 250                 255

Glu Ser Gly Leu Arg Val Leu Ala Arg Asn Pro Glu Thr Thr Leu Gln
            260                 265                 270

Val Trp Ser Ala Asp Tyr Gly Tyr Pro Gly Glu Gly Leu Tyr Arg Glu
        275                 280                 285

Phe His Arg Lys Asp Pro Leu Ser Gly Leu His Trp Arg Val Thr
    290                 295                 300

His Arg Lys Ala Asp Leu Ala Glu Lys Ala Pro Tyr Asp Pro Glu Ala
305                 310                 315                 320

Ala Phe Ala Lys Thr Glu Glu His Ala Arg His Phe Val Gly Leu Leu
                325                 330                 335

Glu Arg Leu Ala Gly Arg His Pro Glu Gly Val Ile Leu Ser Pro Tyr
            340                 345                 350

Asp Ala Glu Leu Phe Gly His Trp Trp Tyr Glu Gly Val Ala Trp Leu
        355                 360                 365

Glu Ala Val Leu Arg Leu Leu Ala Gln Asn Pro Lys Val Arg Pro Val
    370                 375                 380

```
Thr Ala Arg Glu Ala Val Gln Gly Pro Ala Val Arg Thr Ala Leu Pro
385                 390                 395                 400

Glu Gly Ser Trp Gly Arg Gly Asp His Arg Val Trp Leu Asn Glu
            405                 410                 415

Lys Thr Leu Asp Tyr Trp Glu Lys Val Tyr Arg Ala Glu Gly Ala Met
            420                 425                 430

Arg Glu Ala Ala Arg Arg Gly Val Leu Pro Glu Gly Val Leu Arg Gln
        435                 440                 445

Ala Met Arg Glu Leu Leu Leu Glu Ala Ser Asp Trp Pro Phe Leu
    450                 455                 460

Met Glu Thr Gly Gln Ala Glu Ala Tyr Ala Arg Glu Arg Tyr Glu Glu
465                 470                 475                 480

His Ala Arg Ala Phe Phe His Leu Leu Lys Gly Ala Ser Pro Glu Glu
            485                 490                 495

Leu Arg Ala Leu Glu Glu Arg Asp Asn Pro Phe Pro Glu Ala Asp Pro
            500                 505                 510

Arg Leu Tyr Leu Phe Arg Glu Ala
            515                 520
```

METHODS FOR PROMOTING EXTRACELLULAR EXPRESSION OF PROTEINS IN *BACILLUS SUBTILIS* USING A CUTINASE

CROSS-REFERENCE TO RELATED APPLICATIONS

This application claims the benefit of priority to Chinese patent application No. 2020112083956, filed Nov. 3, 2020, the content of which is hereby incorporated by reference in its entirety.

BACKGROUND OF THE INVENTION

Field of the Invention

The invention belongs to the field of genetic engineering, enzyme engineering and microbial engineering. It particularly relates to methods for promoting extracellular expression of proteins in *Bacillus subtilis* (*B. subtilis*) using a cutinase.

Description of the Related Art

Extracellular expression of exogenous proteins can simplify the downstream purification process, save production costs, and has great advantages in large-scale industrial production. An intracellularly localized protein is expressed inside cells, and the cells need to be disrupted by physical or chemical methods to obtain the target protein. The subsequent extraction process is cumbersome and costly, so it has become the goal of researchers to find an effective way to simplify the downstream extraction steps and reduce the purification cost of products.

It was found that cutinase can promote extracellular secretion of proteins in an *Escherichia coli* system without signal peptide mediation. Although the "secretion" mechanism has not been fully understood, it is speculated that this phenomenon is related to the enhanced membrane permeability caused by the limited phospholipid hydrolysis activity of the cutinase. It is also found that, when the cutinase is co-expressed with intracellular proteins in *E. coli*, it can also trigger extracellular release of proteins that are normally localized inside cells. No obvious cell lysis phenomenon is found in this process, and no obvious adverse effect will be generated on the downstream separation and extraction process. When the cutinase and natural intracellularly localized protein are co-expressed in *E. coli*, cutinase can hydrolyze the phospholipid component of the cell membrane to a certain extent and increase the permeability of the cell membrane. In this way, the natural intracellularly localized protein is secreted outside the cell without compromise of cell membrane integrity, which provides a new method for extracellular expression of recombinant intracellularly localized enzyme. However, *E. coli* is not considered a food safety grade strain, so its application in food industry is limited.

*B. subtilis* is a gram-positive bacterium, has the advantages of non-pathogenicity, good environmental compatibility, and does not develop drug resistance easily. *B. subtilis* also has a good fermentation foundation, and its cultivation is simple and fast. *B. subtilis* has been recognized as a food safety grade strain GRAS (Generally recognized as safe) by the U.S. Food and Drug Administration and relevant Chinese authorities. *B. subtilis* is widely used in the production of various industrial enzymes.

When the inventor tried to using the same strategy of co-expressing a cutinase and an intracellular target protein in a *B. subtilis* expression system, the effect of extracellular secretion of the target protein is not good. This is due to the difference in the composition of the cell membrane of *E. coli* and that of *B. subtilis*. Therefore, there is an urgent need to develop a safe and efficient method for extracellular secretion of natural intracellularly localized protein in a *B. subtilis* expression system.

SUMMARY OF THE INVENTION

In view of the aforementioned problems in the use of *E. coli* expression systems to obtain extracellular expression of intracellular proteins, the disclosure aims to provide a safe and efficient method for extracellular secretion of natural intracellularly localized proteins. Firstly, a cutinase mutant is provided, which is obtained by mutating one or more sites at the amino acid residue positions 175, 177, 178, 207, 209, 213 and 214 of a cutinase having the amino acid sequence of SEQ ID NO: 1.

In one embodiment of the invention, the cutinase is derived from *Thermobifida fusca*.

The nucleotide sequence of the cutinase is set forth in SEQ ID NO: 2.

In one embodiment of the invention, the cutinase mutant is a single amino acid mutation obtained by mutating the amino acid at the positions 175, 177, 178, 207, 209, 213 or 214 of the cutinase having the amino acid sequence of SEQ ID NO: 1 to alanine, and is named as: L175A, T177A, I178A, T207A, F209A, I213A and P214A, respectively.

In one embodiment of the invention, the cutinase mutation is a double amino acid mutation L175A/T177A obtained by mutating the leucine (Leu) at position 175 to alanine (Ala) and the threonine (Thr) at position 177 to Ala.

In one embodiment of the invention, the cutinase mutation is a double amino acid mutation T207A/F209A obtained by mutating the Thr at position 207 to Ala and the phenylalanine (Phe) at position 209 to Ala.

In one embodiment of the invention, the cutinase mutation is a double amino acid mutation I213A/P214A obtained by mutating the isoleucine (Ile) at position 213 to Ala and the phenylalanine (Phe) at position 214 to Ala.

In one embodiment of the invention, it provides a gene for encoding a mutant cutinase.

In one embodiment of the invention, it provides a vector carrying the gene encoding the mutant cutinase.

In one embodiment of the invention, it provides a recombinant cell carrying the cutinase mutant gene or the vector containing the cutinase mutant gene.

In one embodiment of the invention, the recombinant cell takes *B. subtilis* as an expression host.

In one embodiment of the invention, it provides a recombinant *B. subtilis* that co-expresses the cutinase mutant and an intracellular protein.

The intracellular protein is an exogenous protein that is synthesized in ribosome and is localized in the cytoplasm with the help of chaperone proteins under the natural condition.

In one embodiment of the invention, the intracellular protein includes but not limited to xylose isomerase, 4,6-α-glucosyltransferase, 4-α-glucosyltransferase, trehalose synthase and branching enzyme.

In one embodiment of the invention, the amino acid sequence of the xylose isomerase is set forth in SEQ ID NO: 3.

In one embodiment of the invention, the nucleotide sequence of the xylose isomerase is set forth in SEQ ID NO: 4.

In one embodiment of the invention, the amino acid sequence of the 4,6-α-glucosyltransferase is set forth in SEQ ID NO: 5.

In one embodiment of the invention, the nucleotide sequence of the 4,6-α-glucosyltransferase is as shown in SEQ ID NO: 6.

In one embodiment of the invention, the amino acid sequence of the 4-α-glucosyltransferase is as shown in SEQ ID NO: 7.

In one embodiment of the invention, the nucleotide sequence of the 4-α-glucosyltransferase is as shown in SEQ ID NO: 8.

In one embodiment of the invention, the amino acid sequence of the trehalose synthase is SEQ ID NO: 9.

In one embodiment of the invention, the amino acid sequence of the branching enzyme is SEQ ID NO: 10.

In one embodiment of the invention, any one of *B. subtilis* WS5, *B. subtilis* 168, *B. subtilis* W600, *B. subtilis* W800 and *B. subtilis* RIK1285 is taken as the expression host.

In one embodiment of the invention, any one of pHY300PLK, PUB110, pBE-S and pWB980 is taken as an expression vector.

In one embodiment of the invention, it provides a method for constructing the recombinant *B. subtilis*, including: linking the gene encoding the cutinase mutant and the gene encoding the intracellular protein to an expression vector to obtain a recombinant expression vector, and then transforming the recombinant expression vector into an expression host.

In one embodiment of the invention, the method includes the following steps:

(1) Linking the genes encoding the cutinase and the intracellular protein with the plasmid pHY300PLK to obtain a recombinant plasmid; using the recombinant plasmid as a template for site-directed mutation, and designing a mutation primer for performing the site-directed mutation; and constructing a recombinant mutant plasmid containing the gene encoding the cutinase mutant;

(2) Transforming the recombinant mutant plasmid obtained in step (1) into *B. subtilis* WS5; and (3) Selecting positive clones in step (2) for performing fermentation culture, centrifugating the fermentation broth and collecting the fermentation supernatant, wherein the fermentation supernatant is the crude solution containing the intracellular protein.

The *B. subtilis* WS5 has been preserved in the China Center for Type Culture Collection on Sep. 29, 2016 with a preservation number of CCTCC NO: M 2016536; and the preservation address is Wuhan University, Wuhan, China.

The *B. subtilis* WS5 is described in the patent application with the publication number of CN106754466A and the application number of 201611025858.9.

In one embodiment of the invention, it provides methods of using the cutinase mutant, the gene there of, or the vector thereof in promoting extracellular expression of the natural intracellularly localized target protein in *B. subtilis*. The method comprises co-expressing genes of the cutinase mutant and the intracellular target protein in different vectors, or linking the cutinase gene and the intracellular target protein gene in the same vector and transfer the vector into a *B. subtilis* to obtain a recombinant *B. subtilis*.

In one embodiment of the invention, the method further comprises performing fermentation of the recombinant *B. subtilis* with the cutinase mutant and the intracellular target protein and obtaining the target protein in the fermentation broth outside *B. subtilis* cells.

In one embodiment of the invention, it provides a method for producing extracellular protein, comprising: inoculating the recombinant *B. subtilis* into a seed medium to obtain a seed liquid; inoculating the seed liquid into a fermentation medium for performing fermentation; and performing centrifugation and collecting the fermentation supernatant containing the target protein.

In one embodiment of the invention, it provides a method for producing extracellular proteins, comprising the following steps: the recombinant *B. subtilis* cells are inoculated into a seed medium and cultured at 35-38° C. and 180-220 rpm for 8-10 hours to obtain a seed liquid, and the seed liquid is then inoculated into a fermentation medium and cultured at 30-37° C. and 180-220 rpm for 20-26 hours.

In one embodiment of the invention, the components of the seed medium include 8-12 g/L peptone, 4-6 g/L yeast powder and 8-12 g/L sodium chloride.

In one embodiment of the invention, the components of the fermentation medium include 20-25 g/L yeast extract, 5-10 g/L soy peptone and 4-6 g/L glycerol; and the initial pH of the fermentation medium is 6-7.

In one embodiment of the invention, it provides methods of using the cutinase mutant, the gene, the vector, the recombinant cells, or the recombinant *B. subtilis* in enzyme production or enzymatic catalytic reaction.

Beneficial Effects (1) The invention provides a method for promoting extracellular secretion of recombinant intracellular enzymes by co-expressing a cutinase mutant in a *B. subtilis* system. Taking xylose isomerase, 4,6-α-glucosyltransferase, 4-α-glucosyltransferase, trehalose synthase and branching enzyme as examples, the method successfully achieves extracellular expression of the xylose isomerase, 4,6-α-glucosyltransferase, 4-α-glucosyltransferase, trehalose synthase and branching enzyme. The invented method can simplify the downstream purification process, save costs and have great advantages in large-scale production of industrial proteins.

(2) When xylose isomerase is expressed alone, the extracellular enzyme activity of the xylose isomerase is not detected. With the technical solution provided by the invention, the maximum extracellular enzyme activity of the xylose isomerase can reach 5.6 U/mL.

(3) When 4,6-α-glucosyltransferase is expressed alone, the extracellular enzyme activity of the 4,6-α-glucosyltransferase is not detected. With the technical solution provided by the invention, the maximum extracellular enzyme activity of the 4,6-α-glucosyltransferase can reach 745.2 U/mL, achieving efficient extracellular secretion of the recombinant intracellular enzyme.

(4) When 4-α-glucosyltransferase is expressed alone, the extracellular enzyme activity of the 4-α-glucosyltransferase is not detected. With the technical solution provided by the invention, the maximum extracellular enzyme activity of the 4-α-glucosyltransferase can reach 11.4 U/mL.

DETAILED DESCRIPTION

The media involved in the following examples are as follows:

LB solid medium: 10 g/L peptone, 5 g/L yeast extract, 10 g/L NaCl and 0.2 g/L agar powder.

LB liquid medium: 10 g/L peptone, 5 g/L yeast extract and 10 g/L NaCl.

Seed medium: 10 g/L peptone, 5 g/L yeast extract and 10 g/L sodium chloride.

Fermentation medium: 24 g/L yeast extract, 12 g/L soy peptone, 5 g/L glycerol, 12.54 g/L $K_2HPO_4$ and 2.31 g/L $KH_2PO_4$; and the initial pH is 6-7.

The detection methods involved in the following examples are as follows:

Detection Method of Enzyme Activity of Xylose Isomerase

100 μL of a solution to be tested was added to a reaction system (containing a 3 mol·$L^{-1}$ substrate, 100 μL of a glucose solution, 100 μL of a 50 mmol·$L^{-1}$ $MgSO_4$ solution, 100 μL of a 0.3 mol·$L^{-1}$ $Na_2HPO_4$—$KH_2PO_4$ buffer with pH 7.5, and 600 μL of $H_2O$). After reacting at 70° C. for 10 min, 1 mL of 0.5 mol·$L^{-1}$ $HClO_4$ was added to stop the reaction. 500 μL of the reaction solution was taken, and 100 μL of a cysteine hydrochloride solution (15 g·$L^{-1}$), 3 mL of 75% concentrated $H_2SO_4$ and 100 μL of a carbazole-alcohol solution were added, and the mixed solution was shaken and mixed well. Color was developed at 60° C. for 10 min. Cooling was performed in an ice bath, and the absorbance was determined at a wavelength of 560 nm (using the inactivated enzyme solution subjected to the same operations as a blank control).

The enzyme activity is defined as the amount of enzyme required to produce 1 μmol of fructose per minute under the above reaction conditions.

Determination Method of Enzyme Activity of 4,6-α-glucosyltransferase (1) Preparation of substrate: 2 mL of distilled water was added to 40 mg of amylose to fully moisten the amylose, and then 2 mL of a 2 M NaOH solution was added. Vortex shaking was performed to fully dissolve the enzyme to prepare an amylose mother liquor. 500 μL of the amylose mother liquor was added with 250 μL of a 2 M HCl solution, and then 3250 μL of a phosphoric acid-citric acid buffer (pH 7.0) was added to prepare a 0.125% substrate.

(2) Preparation of iodine color solution: 0.26 g of iodine and 2.60 g of potassium iodide were put in a 10 mL volumetric flask, add water to the volumetric flask to the mark (prepared 3 days in advance to ensure that the iodine was completely dissolved) to obtain Lugol's iodine solution. When it is time to perform the assay, 100 μL of the Lugol's iodine solution was added to 50 μL of a 2 M HCl solution, and then water was added to 26 mL to prepare the iodine color solution.

(3) 200 μL of the substrate prepared in step (1) was taken in a 1.5 mL centrifuge tube and placed in a warm bath at 35° C. for 10 min. 200 μL of an enzyme solution to be tested was added and reacted at 35° C. for 10 min. After the reaction, 200 μL of the reaction solution was added to 3800 μL of the iodine color solution for color development for 5 min, and the absorbance at 660 nm was determined by a spectrophotometer.

As a control, 200 μl buffer, instead of the enzyme solution, was added to 3800 μL of the iodine color solution for color development.

The unit of enzyme activity is defined as: the absorbance value decreased by one percent per unit time is a unit of enzyme activity.

Detection Method of Enzyme Activity of Trehalose Synthase:

400 μL of an enzyme solution diluted to a suitable multiple was taken and 400 μL of a 5% (w/v) maltose solution prepared with a phosphate buffer (20 mmol/L, pH7.0) was added to obtain a mixed solution. The mixed solution was reacted at 30° C. for 30 min, then the enzyme reaction was terminated in a boiling water bath for 10 min, and the content of trehalose produced was determined by HPLC.

The HPLC detection conditions were: a mobile phase contained acetonitrile and water in a ratio of 80:20, the flow rate was 0.8 mL/min, the column temperature was 40° C., and a $NH_2$ column and a differential detector were used.

Definition of enzyme activity: Under the above reaction conditions, the amount of enzyme required to form 1 μmol of trehalose per minute is defined as 1 unit of enzyme activity.

Detection Method of Enzyme Activity of Branching Enzyme:

(1) Preparation of substrate: 0.01 g of amylose (0.1 g of amylopectin) and 0.2 mL of 96% ethanol were taken, 0.5 mL of a 2 mol·$L^{-1}$ NaOH solution was added after 3-4 min, 10 mL of water was added, the mixed solution was stirred for 10 min to dissolve the starch, then 0.5 mL of a 2 mol·$L^{-1}$ HCL solution was added, and a phosphate buffer (50 mmol·$L^{-1}$, pH 6.5) was added to volume to 10 mL to adjust the pH (prepared when used).

(2) Preparation of termination reaction solution: Lugol's iodine solution (mother liquor): 0.26 g of iodine and 2.60 g of potassium iodide were dissolved in a 10 mL volumetric flask, and stored at room temperature and protected from light. 0.1 mL of the Lugol's iodine solution was added, and 50 μL of a 2 mol·$L^{-1}$ hydrochloric acid solution was added, and water was added to volume to 26 mL (prepared when used).

(3) 50 μL of a crude enzyme solution was taken and 50 μL of a substrate was added, and the mixed solution was placed in a water bath at 60° C. for 30 min. After adding 2 mL of the termination reaction solution, the absorbance at 660 nm was determined after being placed at room temperature for 20 min.

Definition of enzyme activity: At room temperature, the absorbance value at 660 nm decreased by 1% per minute is as a unit of enzyme activity.

Detection Method of 4-α-glucosyltransferase

25 μL of a 0.02% (w·$v^{-1}$) potato amylose solution (dissolved in 90% dimethyl sulfoxide) was taken in a test tube, and preheated in a water bath at 70° C. for 10 min. 25 μL of a diluted enzyme solution (dissolved in a 50 mmol·$L^{-1}$ $Na_2HPO_4$-citrate buffer with pH 5.5) was added, and the mixed solution was shaken and mixed well. After reacting at 70° C. for 30 min, 1 mL of an iodine solution (0.1 mL of original iodine solution+0.1 mL of 1 N HCl, diluted to 26 mL) was added to terminate the reaction. The original iodine solution was 26% KI+2.6% $I_2$.

Definition of unit of enzyme activity: Under the enzyme activity measurement system, the amount of enzyme required to decrease the absorbance value A660 by 0.1 per minute.

Example 1: Construction of Recombinant Plasmid (1) Plasmid pHYPMLd4P (the plasmid contains pullulanase puL and chaperone protein prsA genes, and the construction method is recorded in the doctoral dissertation "Modification of *Bacillus subtilis* Strain, Promoter Optimization and High-Level Expression of Pullulanase", of Zhang Kang, Jiangnan University, 2018) stored in the laboratory was used as a template to design forward and reverse primers, respectively:

```
pHY300PLK-F1:
5'-AAGCTTGGTAATAAAAAAACACCTCC-3';

pHY300PLK-R1:
5'-TCTTGACACTCCTTATTTGATTTTT-3';
```

An expression vector pHY300PLK-prsA fragment was amplified.

(2) Plasmid xylA/pET24a (+) (the construction method of the plasmid is recorded in Chinese Patent ZL201210581801.2) stored in the laboratory was used as a template to design forward and reverse primers, respectively:

```
xylA-F:
5'-GGAGTGTCAAGAATGAGCAACTACCAGCCCACAC-3';

xylA-R:
5'-TTTATTACCAAGCTTTTAGCGCACGCCCAGGAGGTAG-3';
```

A xylose isomerase gene fragment was amplified.

(3) The expression vector pHY300PLK-prsA fragment obtained in step (1) and the xylose isomerase gene fragment obtained in step (2) were linked by Infusion. The linked product was transformed into an *E. coli* JM109 competent cell to obtain a transformed product. The plasmid in the transformed product was extracted and verified by Hind III restriction enzyme digestion and sequenced to obtain the recombinant plasmid pHY300PLK-xylA-prsA.

The recombinant plasmid pHY300PLK-xylA-prsA was used as a template to design forward and reverse primers, respectively:

```
pHY300PLK-F2:
5'-GAGCTCGGTACCCTCGAGGG-3';

pHY300PLK-R2:
5'-ACGCGTCCCTCTCCTTTTGC-3';
```

An expression vector pHY300PLK-xylA fragment was amplified.

(4) Plasmid pET20b-Tfu_0883 (the construction method of the plasmid is recorded in Chen S, Tong X, Woodard R W, Du G C, Wu J, Chen J, Identification and Characterization of Bacterial Cutinase, Journal of Biological Chemistry, 2008, 283(28):25854-25862) stored in the laboratory was used as a template to design forward and reverse primers, respectively:

```
cut-F:
5'-AGGAGAGGGACGCGTATGGCCAACCCCTACGAGCGCGG-3';

cut-R:
5'-GAGGGTACCGAGCTCTTAGAACGGGCAGGTGGAGCG-3';
```

A cutinase gene cut was amplified.

The expression vector pHY300PLK-xylA fragment obtained in step (3) and the cutinase gene fragment were linked by Infusion. The linked product was transformed into an *E. coli* JM109 competent cell to obtain a transformed product. The plasmid in the transformed product was extracted and verified by Hind III restriction enzyme digestion and sequenced to obtain the recombinant plasmid pHY300PLK-xylA-cut.

(5) The recombinant plasmid pHYPMLd4 (the plasmid contains pullulanase pul gene, and the construction method is recorded in the doctoral dissertation "Modification of *Bacillus subtilis* Strain, Promoter Optimization and High-Level Expression of Pullulanase", of Zhang Kang, Jiangnan University, 2018) was used as a template, and an expression vector pHY300PLK fragment was amplified using the forward and reverse primers (pHY300PLK-F1 and pHY300PLK-R1). Plasmid xylA/pET24a (+) (disclosed in a patent with the patent number of ZL201210581801.2) stored in the laboratory was used as a template, and a xylose isomerase gene fragment was amplified using the forward and reverse primers (xylA-F and xylA-R). The expression vector pHY300PLK fragment and the xylose isomerase gene fragment were linked by Infusion. The linked product was transformed into an *E. coli* JM109 competent cell to obtain a transformed product. The plasmid in the transformed product was extracted and verified by Hind III restriction enzyme digestion and sequenced to obtain the recombinant plasmid pHY300PLK-xylA.

Example 2: Construction of Cutinase Mutant

The recombinant plasmid pHY300PLK-xylA-cut obtained in step (4) of Example 1 was used as a template, and according to the gene sequences of cutinase, primers introducing mutations of L175A/T177A, T207A/F209A, I213A/P214A, I178A, L175A, T177A, T207A, F209A, I213A and P214A were designed and synthesized. The cutinase genes were subjected to site-directed mutation and verified by sequencing to obtain recombinant expression vectors containing the cutinase mutant genes: pHY300PLK-xylA-L175A/T177A, pHY300PLK-xylA-T207A/F209A, pHY300PLK-xylA-I213A/P214A, pHY300PLK-xylA-I178A, pHY300PLK-xylA-L175A, pHY300PLK-xylA-T177A, pHY300PLK-xylA-T207A, pHY300PLK-xylA-F209A, pHY300PLK-xylA-I213A, pHY300PLK-xylA-P214A.

The site-directed mutation primer introducing the L175A/T177A mutation was:

```
L175A/T177A-F:
5'-GATCATCGGGGCCGACGCAGACGCGATCGCGCCGGTCG-3'

L175A/T177A-R:
5'-CGACCGGCGCGATCGCGTCTGCGTCGGCCCCGATGATC-3'
```

The site-directed mutation primer introducing the T207A/F209A mutation was:

```
T207A/F209A-F:
5'-GGAGCTGGACGGCGCAGCCCACGCAGCCCCGAACATCCCC-3'

T207A/F209A-R:
5'-GGGGATGTTCGGGGCTGCGTGGGCTGCGCCGTCCAGCTCC-3'
```

The site-directed mutation primer introducing the I213A/P214A mutation was:

```
I213A/P214A-F:
5'-CCACTTCGCCCCGAACGCCGCCAACAAGATCATCGG-3'

I213A/P214A-R:
5'-CCGATGATCTTGTTGGCGGCGTTCGGGGCGAAGTGG-3'
```

The site-directed mutation primer introducing the I178A mutation was:

```
I178A-F:
5'-CCGACCTCGACACGGCAGCGCCGGTCGCCAC-3'

I178A-R:
5'-GTGGCGACCGGCGCTGCCGTGTCGAGGTCGG-3'
```

The site-directed mutation primer introducing the L175A mutation was:

```
L175A-F:
5'-GATCATCGGGGCCGACGCAGACACGATCGCGCCG-3'

L175A-R:
5'-CGGCGCGATCGTGTCTGCGTCGGCCCCGATGATC-3'
```

The site-directed mutation primer introducing the T177A mutation was:

```
T177A-F:
5'-GGGCCGACCTCGACGCGATCGCGCCGGTCG-3'

T177A-R:
5'-CGACCGGCGCGATCGCGTCGAGGTCGGCCC-3'
```

The site-directed mutation primer introducing the T207A mutation was:

```
T207A-F:
5'-GGAGCTGGACGGCGCAGCCCACTTCGCCCCGAAC-3'

T207A-R:
5'-GTTCGGGGCGAAGTGGGCTGCGCCGTCCAGCTCC-3'
```

The site-directed mutation primer introducing the F209A mutation was:

```
F209A-F:
5'-GCTGGACGGCGCAACCCACGCAGCCCCGAACATCCCC-3'

F209A-R:
5'-GGGGATGTTCGGGGCTGCGTGGGTTGCGCCGTCCAGC-3'
```

The site-directed mutation primer introducing the I213A mutation was:

```
I213A-F:
5'-CCACTTCGCCCCGAACGCCCCCAACAAGATCATCGG-3'

I213A-R:
5'-CCGATGATCTTGTTGGGGGCGTTCGGGGCGAAGTGG-3'
```

The site-directed mutation primer introducing the P214A mutation was:

```
P214A-F:
5'-CCACTTCGCCCCGAACATCGCCAACAAGATCATCGG-3'

P214A-R:
5'-CCGATGATCTTGTTGGCGATGTTCGGGGCGAAGTGG-3'
```

Example 3: Construction of Recombinant Bacteria Co-Expressing Cutinase Mutant and Xylose Isomerase (1) Preparation of Competent Cells Cryopreserved *B. subtilis* WS5 was taken by dipping with an inoculating loop, then streaked on an LB solid medium, and cultured overnight at 37° C. for activation. A single colony was picked, inoculated in 10 mL of LB liquid medium, and cultured overnight at 37° C. and 200 rpm for 8 h to obtain a culture solution. 2.5 mL of the culture solution was transferred to 40 mL of LB liquid medium containing 0.5 M sorbitol, and cultured at 37° C. and 200 rpm for 4-5 h to obtain a bacterial solution. The obtained bacterial solution was placed in an ice-water bath for 10 min, and then centrifuged at 4° C. and 5000 rpm for 5 min, and bacterial cells were collected. The bacterial cells were resuspended in 50 mL of a pre-cooled electroporation transformation buffer, and centrifuged at 4° C. and 5000 rpm for 5 min. The supernatant was removed, and the bacterial cells were rinsed 4 times according to the above steps. The washed bacterial cells were resuspended in 1 mL of the electroporation transformation medium and dispensed into 1.5 mL EP tubes with 200 μL per tube to obtain the competent cells.

(2) Transformation of Competent Cells

The recombinant plasmids obtained in Examples 1 and 2 were added to the competent cells obtained in step (1). After being placed in an ice bath for 18 min, the competent cells and the recombinant plasmids were added to a pre-cooled electroporation cuvette (2 mm) and shocked (at 2.4 kv, 25 μF, 200Ω) once. After the electric shock is completed, 1 mL of a pre-cooled RM medium (RM medium components: peptone 10 g/L, yeast powder 5 g/L, NaCl 10 g/L, sorbitol 91 g/L and mannitol 69 g/L) was added immediately. After resuscitating at 37° C. and 200 rpm for 3 h, the competent cells were applied to a plate containing tetracycline resistance (50 μg/mL) to obtain recombinant bacteria:

*Bacillus subtilis* WS5/pHY300PLK-xylA, *Bacillus subtilis* WS5/pHY300PLK-xylA-cut, *Bacillus subtilis* WS5/pHY300PLK-xylA-L175A/T177A, *Bacillus subtilis* WS5/pHY300PLK-xylA-T207A/F209A, *Bacillus subtilis* WS5/pHY300PLK-xylA-I213A/P214A, *Bacillus subtilis* WS5/pHY300PLK-xylA 4178A, *Bacillus subtilis* WS5/pHY300PLK-xylA-L175A, *Bacillus subtilis* WS5/pHY300PLK-xylA-T177A, *Bacillus subtilis* WS5/pHY300PLK-xylA-T207A, *Bacillus subtilis* WS5/pHY300PLK-xylA-F209A, *Bacillus subtilis* WS5/pHY300PLK-xylA4213A, *Bacillus subtilis* WS5/pHY300PLK-xylA-P214A.

Example 4: Production of Xylose Isomerase by Shake Flask Fermentation (1) The recombinant *B. subtilis* strains obtained in Example 3 were inoculated into the seed culture media, and cultured at 35-38° C. and 180-220 rpm for 8-10 h to obtain the seed liquids.

(2) The seed liquids obtained in step (1) were transferred to the fermentation media at an inoculum concentration of 5% (v/v), and cultured at 33° C. and 200 rpm for 24 h. Then the culture solutions were centrifuged at 12000 r·min$^{-1}$ for 10 min to obtain fermentation supernatant. The fermentation supernatant was tested for the enzyme activity of xylose isomerase. The test results are shown in Table 1:

TABLE 1

Enzyme activity of xylose isomerase in fermentation supernatant

| Recombinant bacteria | Enzyme activity of xylose isomerase expressed (U/mL) |
|---|---|
| *Bacillus subtilis* WS5/pHY300PLK-xylA | 0 |
| *Bacillus subtilis* WS5/pHY300PLK-xylA-cut | 0.8 |
| *Bacillus subtilis* WS5/pHY300PLK-xylA-L175A/T177A | 4.2 |
| *Bacillus subtilis* WS5/pHY300PLK-xylA-T207A/F209A | 5.3 |
| *Bacillus subtilis* WS5/pHY300PLK-xylA-I213A/P214A | 5.6 |
| *Bacillus subtilis* WS5/pHY300PLK-xylA-I178A | 3.8 |
| *Bacillus subtilis* WS5/pHY300PLK-xylA-L175A | 3.3 |
| *Bacillus subtilis* WS5/pHY300PLK-xylA-T177A | 2.1 |
| *Bacillus subtilis* WS5/pHY300PLK-xylA-T207A | 3.2 |
| *Bacillus subtilis* WS5/pHY300PLK-xylA-F209A | 4.5 |
| *Bacillus subtilis* WS5/pHY300PLK-xylA-I213A | 3.6 |
| *Bacillus subtilis* WS5/pHY300PLK-xylA-P214A | 3.8 |

It can be seen from the test results that when the xylose isomerase was expressed alone, the extracellular enzyme activity of the xylose isomerase was not detected. When co-expressed with the cutinase or mutants thereof, the extracellular enzyme activity was detected, proving that the technical solution of the disclosure realizes the extracellular secretion of the xylose isomerase in *B. subtilis*. At the same time, the enzyme activity when the xylose isomerase and cutinase mutant I213A/P214A were co-expressed is 7 times the enzyme activity when the xylose isomerase and wild-type cutinase were co-expressed.

Example 5: Co-Expression of Cutinase Mutants Promotes Extracellular Expression of 4,6-α-glucosyltransferase (1) Recombinant plasmids pHY300PLK-gtfB, pHY300PLK-gtfB-cut, pHY300PLK-gtfB-L175A/T177A, pHY300PLK-gtfB-T207A/F209A, pHY300PLK-gtfB-I213A/P214A, pHY300PLK-gtfB-I178A, pHY300PLK-gtfB-L175A, pHY300PLK-gtfB-T177A, pHY300PLK-gtfB-T207A, pHY300PLK-gtfB-F209A, pHY300PLK-gtfB-I213A and pHY300PLK-gtfB-P214A were constructed by the methods of Examples 1-3 and transformed into *B. subtilis* WS5 to obtain recombinant bacteria:

*Bacillus subtilis* WS5/pHY300PLK-gtfB, *Bacillus subtilis* WS5/pHY300PLK-gtfB-cut, *Bacillus subtilis* WS5/pHY300PLK-gtfB-L175A/T177A, *Bacillus subtilis* WS5/pHY300PLK-gtfB-T207A/F209A, *Bacillus subtilis* WS5/pHY300PLK-gtfB-I213A/P214A, *Bacillus subtilis* WS5/pHY300PLK-gtfB-I178A, *Bacillus subtilis* WS5/pHY300PLK-gtfB-L175A, *Bacillus subtilis* WS5/pHY300PLK-gtfB-T177A, *Bacillus subtilis* WS5/pHY300PLK-gtfB-T207A, *Bacillus subtilis* WS5/pHY300PLK-gtfB-F209A, *Bacillus subtilis* WS5/pHY300PLK-gtfB-I213A, *Bacillus subtilis* WS5/pHY300PLK-gtfB-P214A.

(2) The recombinant *B. subtilis* strains were inoculated into the seed culture media, and cultured at 35-38° C. and 180-220 rpm for 8-10 h to obtain the seed liquids.

(3) The seed liquids obtained in step (2) were transferred to the fermentation media at an inoculum concentration of 5% (v/v), and cultured at 33° C. and 200 rpm for 24 h. Then the culture solutions were centrifuged at 12000 r·min$^{-1}$ for 10 min to obtain fermentation supernatant. The fermentation supernatant was tested for the enzyme activity of 4,6-α-glucosyltransferase. The test results are shown in Table 2:

TABLE 2

Enzyme activity of 4,6-a-glucosyltransferase in fermentation supernatant

| Recombinant bacteria | Enzyme activity of 4,6-a-glucosyltransferase expressed (U/mL) |
|---|---|
| *Bacillus subtilis* WS5/pHY300PLK-gtfB | 0 |
| *Bacillus subtilis* WS5/pHY300PLK-gtfB-cut | 123.6 |
| *Bacillus subtilis* WS5/pHY300PLK-gtfB-L175A/T177A | 458.9 |
| *Bacillus subtilis* WS5/pHY300PLK-gtfB-T207A/F209A | 652.8 |
| *Bacillus subtilis* WS5/pHY300PLK-gtfB-I213A/P214A | 745.2 |
| *Bacillus subtilis* WS5/pHY300PLK-gtfB-I178A | 428.6 |
| *Bacillus subtilis* WS5/pHY300PLK-gtfB-L175A | 136.2 |
| *Bacillus subtilis* WS5/pHY300PLK-gtfB-T177A | 325.8 |
| *Bacillus subtilis* WS5/pHY300PLK-gtfB-T207A | 232.8 |
| *Bacillus subtilis* WS5/pHY300PLK-gtfB-F209A | 465.3 |
| *Bacillus subtilis* WS5/pHY300PLK-gtfB-I213A | 389.4 |
| *Bacillus subtilis* WS5/pHY300PLK-gtfB-P214A | 486.6 |

It can be seen from the test results that when the 4,6-α-glucosyltransferase was expressed alone (*Bacillus subtilis* WS5/pHY300PLK-gtfB), the extracellular enzyme activity of the 4,6-α-glucosyltransferase was not detected.

The enzyme activity when the 4,6-α-glucosyltransferase and cutinase mutant I213A/P214A were co-expressed (*Bacillus subtilis* WS5/pHY300PLK-gtfB-I213A/P214A) is 6 times the enzyme activity when the 4,6-α-glucosyltransferase and wild-type cutinase were co-expressed (*Bacillus subtilis* WS5/pHY300PLK-gtfB-cut).

Example 6: Co-Expression of Cutinase Mutants Promotes Extracellular Expression of 4-α-glucosyltransferase (1) Recombinant plasmids pHY300PLK-4GT, pHY300PLK-4GT-cut, pHY300PLK-4GT-L175A/T177A, pHY300PLK-4GT-T207A/F209A, pHY300PLK-4GT-I213A/P214A, pHY300PLK-4GT-I178A, pHY300PLK-4GT-L175A, pHY300PLK-4GT-T177A, pHY300PLK-4GT-T207A, pHY300PLK-4GT-F209A, pHY300PLK-4GT 4213A and pHY300PLK-4GT-P214A were constructed by the methods of Examples 1-3 and transformed into *B. subtilis* WS5 to obtain recombinant bacteria:

*Bacillus subtilis* WS5/pHY300PLK-4GT, *Bacillus subtilis* WS5/pHY300PLK-4GT-cut, *Bacillus subtilis* WS5/pHY300PLK-4GT-L175A/T177A, *Bacillus subtilis* WS5/pHY300PLK-4GT-T207A/F209A, *Bacillus subtilis* WS5/pHY300PLK-4GT I213A/P214A, *Bacillus subtilis* WS5/pHY300PLK-4GT-I178A, *Bacillus subtilis* WS5/pHY300PLK-4GT-L175A, *Bacillus subtilis* WS5/pHY300PLK-4GT-T177A, *Bacillus subtilis* WS5/pHY300PLK-4GT-T207A, *Bacillus subtilis* WS5/pHY300PLK-4GT-F209A, *Bacillus subtilis* WS5/pHY300PLK-4GT 4213A, *Bacillus subtilis* WS5/pHY300PLK-4GT-P214A.

(2) The recombinant *B. subtilis* strains were inoculated into the seed culture media, and cultured at 35-38° C. and 180-220 rpm for 8-10 h to obtain the seed liquids.

(3) The seed liquids obtained in step (2) were transferred to the fermentation media at an inoculum concentration of 5% (v/v), and cultured at 33° C. and 200 rpm for 24 h. Then the culture solutions were centrifuged at 12000 r·min$^{-1}$ for 10 min to obtain fermentation supernatant. The fermentation supernatant was tested for the enzyme activity of 4-α-glucosyltransferase. The test results are shown in Table 3:

TABLE 3

Enzyme activity of 4-a-glucosyltransferase in fermentation supernatant

| Recombinant bacteria | Enzyme activity of 4-a-glucosyltransferase expressed (U/mL) |
|---|---|
| *Bacillus subtilis* WS5/pHY300PLK-4GT | 0 |
| *Bacillus subtilis* WS5/pHY300PLK-4GT-cut | 2.5 |
| *Bacillus subtilis* WS5/pHY300PLK-4GT-L175A/T177A | 6.6 |
| *Bacillus subtilis* WS5/pHY300PLK-4GT-T207A/F209A | 11.4 |
| *Bacillus subtilis* WS5/pHY300PLK-4GT-I213A/P214A | 10.5 |
| *Bacillus subtilis* WS5/pHY300PLK-4GT-I178A | 8.2 |
| *Bacillus subtilis* WS5/pHY300PLK-4GT-L175A | 6.0 |
| *Bacillus subtilis* WS5/pHY300PLK-4GT-T177A | 4.2 |
| *Bacillus subtilis* WS5/pHY300PLK-4GT-T207A | 7.8 |
| *Bacillus subtilis* WS5/pHY300PLK-4GT-F209A | 7.3 |
| *Bacillus subtilis* WS5/pHY300PLK-4GT-I213A | 7.4 |
| *Bacillus subtilis* WS5/pHY300PLK-4GT-P214A | 8.6 |

It can be seen from the test results that when the 4-α-glucosyltransferase was expressed alone (*Bacillus subtilis* WS5/pHY300PLK-4GT), the extracellular enzyme activity of the 4-α-glucosyltransferase was not detected.

The enzyme activity when the 4-α-glucosyltransferase and cutinase mutant T207A/F209A were co-expressed (*Bacillus subtilis* WS5/pHY300PLK-4GT-T207A/F209A) is 4.6 times the enzyme activity when the 4-α-glucosyltransferase and wild-type cutinase were co-expressed (*Bacillus subtilis* WS5/pHY300PLK-4GT-cut).

Example 7: Co-Expression of Cutinase Mutants Promotes Extracellular Expression of Trehalose Synthase (1) Recombinant plasmids were constructed by the methods of Examples 1-3 and transformed into *B. subtilis* WS5 to obtain recombinant bacteria:

*Bacillus subtilis* WS5/pHY300PLK-treS, *Bacillus subtilis* WS5/pHY300PLK-treS-cut, *Bacillus subtilis* WS5/pHY300PLK-treS-L175A/T177A, *Bacillus subtilis* WS5/pHY300PLK-treS-T207A/F209A, *Bacillus subtilis* WS5/pHY300PLK-treS-I213A/P214A, *Bacillus subtilis* WS5/pHY300PLK-treS-I178A, *Bacillus subtilis* WS5/pHY300PLK-treS-L175A, *Bacillus subtilis* WS5/pHY300PLK-treS-T177A, *Bacillus subtilis* WS5/pHY300PLK-treS-T207A, *Bacillus subtilis* WS5/pHY300PLK-treS-F209A, *Bacillus subtilis* WS5/pHY300PLK-treS-I213A, *Bacillus subtilis* WS5/pHY300PLK-treS-P214A (wherein the literature involved in plasmid construction is: doctoral dissertation "Study on *B. subtilis* Strain Modification, Promoter Optimization and Efficient Preparation of Pullulanase" of Zhang Kang, Jiangnan University, 2018; Luo Feng, Duan Xuguo, Su Lingqia, Wu Jing, Cloning Expression and Fermentation Optimization of *Thermobifida fusca* Trehalose Synthase Gene, Journal of Chinese Biotechnology, 2013, 33 (8): 98-104).

(2) The recombinant *B. subtilis* strains were inoculated into the seed culture media, and cultured at 35-38° C. and 180-220 rpm for 8-10 h to obtain the seed liquids.

(3) The seed liquids obtained in step (2) were transferred to the fermentation media at an inoculum concentration of 5% (v/v), and cultured at 33° C. and 200 rpm for 24 h. Then the culture solutions were centrifuged at 12000 r·min$^{-1}$ for 10 min to obtain fermentation supernatant. The fermentation supernatant was tested for the enzyme activity of trehalose synthase. When the trehalose synthase was expressed alone, the extracellular enzyme activity of the trehalose synthase was not detected. When co-expressed with the cutinase or mutants thereof, the extracellular enzyme activity was detected.

Example 8: Co-Expression of Cutinase Mutants Promotes Extracellular Expression of Branching Enzyme (1) Recombinant plasmids were constructed by the methods of Examples 1-3 and transformed into *B. subtilis* WS5 to obtain recombinant bacteria:

*Bacillus subtilis* WS5/pHY300PLK-TtSBE, *Bacillus subtilis* WS5/pHY300PLK-TtSBE-cut, *Bacillus subtilis* WS5/pHY300PLK-TtSBE-L175A/T177A, *Bacillus subtilis* WS5/pHY300PLK-TtSBE-T207A/F209A, *Bacillus subtilis* WS5/pHY300PLK-TtSBE-I213A/P214A, *Bacillus subtilis* WS5/pHY300PLK-TtSBE-I178A, *Bacillus subtilis* WS5/pHY300PLK-TtSBE-L175A, *Bacillus subtilis* WS5/pHY300PLK-TtSBE-T177A, *Bacillus subtilis* WS5/pHY300PLK-TtSBE-T207A, *Bacillus subtilis* WS5/pHY300PLK-TtSBE-F209A, *Bacillus subtilis* WS5/pHY300PLK-TtSBE-I213A, *Bacillus subtilis* WS5/pHY300PLK-TtSBE-P214A (wherein the literature involved in plasmid construction is: Master's thesis of Liu Jun, Jiangnan University, 2017).

(2) The recombinant *B. subtilis* strains were inoculated into the seed culture media, and cultured at 35-38° C. and 180-220 rpm for 8-10 h to obtain the seed liquids.

(3) The seed liquids obtained in step (2) were transferred to the fermentation media at an inoculum concentration of 5% (v/v), and cultured at 33° C. and 200 rpm for 24 h. Then the culture solutions were centrifuged at 12000 r·min$^{-1}$ for 10 min to obtain fermentation supernatant. The fermentation supernatant was tested for the enzyme activity of branching enzyme. When the branching enzyme was expressed alone, the extracellular enzyme activity of the branching enzyme was not detected. When co-expressed with the cutinase or mutants thereof, the extracellular enzyme activity was detected.

What is claimed is:

1. A cutinase mutant, which is a cutinase having the amino acid sequence of SEQ ID NO: 1 except having I213A and P214A substitutions.

2. A method for extracellularly producing an exogenous protein, comprising:
   a) inoculating a recombinant *B. subtilis* coexpressing the cutinase mutant of claim 1 and an exogenous intracellularly located protein into a seed medium to obtain a seed liquid;
   b) inoculating the seed liquid into a fermentation medium for performing fermentation to obtain a fermentation broth; and
   c) centrifuging the fermentation broth and obtaining the exogenous protein in the fermentation supernatant of the centrifuged fermentation broth.

3. The method of claim 2, wherein the recombinant *B. subtilis* are inoculated into the seed medium and cultured at 35-38° C., 180-220 rpm for 8-10 hours to obtain the seed liquid, and the seed liquid is inoculated into the fermentation medium and cultured at 30-37° C., 180-220 rpm for 20-26 hours.

4. The method of claim 2, wherein the seed medium comprises 8-12 g/L peptone, 4-6 g/L yeast extract and 8-12 g/L sodium chloride.

5. The method of claim 2, wherein the fermentation medium comprises 20-25 g/L yeast extract, 5-10 g/L soy peptone and 4-6 g/L glycerol, and the initial pH of the fermentation medium is 6-7.

* * * * *